United States Patent
Sherwood et al.

(10) Patent No.: US 9,959,978 B2
(45) Date of Patent: *May 1, 2018

(54) SYSTEMS AND METHODS FOR ENHANCED DIELECTRIC PROPERTIES FOR ELECTROLYTIC CAPACITORS

(71) Applicant: Cardiac Pacemakers, Inc., St. Paul, MN (US)

(72) Inventors: Gregory J. Sherwood, North Oaks, MN (US); Michael J. Root, Lino Lakes, MN (US); Mary M. Byron, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/044,643

(22) Filed: Feb. 16, 2016

(65) Prior Publication Data

US 2016/0163467 A1 Jun. 9, 2016

Related U.S. Application Data

(63) Continuation of application No. 13/038,987, filed on Mar. 2, 2011, now Pat. No. 9,275,801.

(51) Int. Cl.
*H01G 9/07* (2006.01)
*H01G 9/00* (2006.01)
(Continued)

(52) U.S. Cl.
CPC ............. *H01G 9/07* (2013.01); *H01G 9/0032* (2013.01); *H01G 9/035* (2013.01); *H01G 9/145* (2013.01);
(Continued)

(58) Field of Classification Search
CPC ............. H01G 4/018; H01G 4/10; H01G 9/07
See application file for complete search history.

(56) References Cited

U.S. PATENT DOCUMENTS 5,018,180 A    5/1991   Shoulders
5,963,418 A    10/1999   Greenwood, Jr. et al.
(Continued)

OTHER PUBLICATIONS

"http://en.wikipedia.org/wiki/Atomic_layer_deposition" May 31, 2009.*

(Continued)

*Primary Examiner* — Michael Carey
*Assistant Examiner* — Natasha Patel
(74) *Attorney, Agent, or Firm* — Schwegman Lundberg & Woessner, P.A.

(57) ABSTRACT

This disclosure relates to methods and apparatus for enhanced dielectric properties for electrolytic capacitors to store energy in an implantable medical device. One aspect of the present subject matter includes a method for manufacturing a capacitor adapted to be disposed in an implantable device housing. An embodiment of the method includes providing a dielectric comprising aluminum oxide and doping the aluminum oxide with an oxide having a dielectric constant greater than aluminum oxide. Doping the aluminum oxide includes using sol-gel based chemistry, electrodeposition or atomic layer deposition (ALD) in various embodiments.

20 Claims, 7 Drawing Sheets

Related U.S. Application Data

(60) Provisional application No. 61/315,586, filed on Mar. 19, 2010.

(51) Int. Cl.
  *H01G 9/035* (2006.01)
  *H01G 9/145* (2006.01)
  *A61N 1/375* (2006.01)
  *A61N 1/378* (2006.01)

(52) U.S. Cl.
  CPC ............ *A61N 1/375* (2013.01); *A61N 1/3782* (2013.01); *Y10T 29/435* (2015.01)

(56) References Cited

U.S. PATENT DOCUMENTS

| | | |
|---|---|---|
| 6,096,414 A | 8/2000 | Young |
| 6,159,819 A | 12/2000 | Tsai et al. |
| 6,774,050 B2 | 8/2004 | Ahn et al. |
| 6,843,895 B2 | 1/2005 | Bakhir et al. |
| 6,858,865 B2 | 2/2005 | Ahn et al. |
| 7,276,729 B2 | 10/2007 | Ahn et al. |
| 7,339,191 B2 | 3/2008 | Ahn et al. |
| 7,342,773 B2 | 3/2008 | Harrington et al. |
| 7,361,928 B2 | 4/2008 | Ahn et al. |
| 7,750,344 B2 | 7/2010 | Ahn et al. |
| 9,275,801 B2 | 3/2016 | Sherwood et al. |
| 2002/0135048 A1 | 9/2002 | Ahn et al. |
| 2003/0072126 A1 | 4/2003 | Bhattacharyya |
| 2003/0169560 A1 | 9/2003 | Welsch et al. |
| 2004/0114310 A1 | 6/2004 | Katsir et al. |
| 2004/0188269 A1 | 9/2004 | Harrington et al. |
| 2006/0043448 A1* | 3/2006 | Basceri ............... H01L 27/1085 257/296 |
| 2006/0079050 A1 | 4/2006 | Cahalen et al. |
| 2007/0139860 A1 | 6/2007 | Hoerpel et al. |
| 2009/0034156 A1 | 2/2009 | Yamamoto et al. |
| 2009/0127656 A1 | 5/2009 | Basceri et al. |
| 2010/0123996 A1* | 5/2010 | Imanaka .................. H01G 4/10 361/313 |
| 2011/0230924 A1 | 9/2011 | Sherwood et al. |

OTHER PUBLICATIONS https://web.archive.org/web/20091201123826/https://en.wikipedia.org/wiki/Electroplating Nov. 30, 2009.*

"http://en.wikipedia.org/wiki/Transition_metal" Jan. 28, 2005.*

"U.S. Appl. No. 13/038,987, Advisory Action dated Jan. 23, 2015", 2 pgs.

"U.S. Appl. No. 13/038,987, Final Office Action dated Feb. 7, 2014", 7 pgs.

"U.S. Appl. No. 13/038,987, Final Office Action dated Jun. 16, 2015", 8 pgs.

"U.S. Appl. No. 13/038,987, Final Office Action dated Nov. 5, 2014", 9 pgs.

"U.S. Appl. No. 13/038,987, Non Final Office Action dated Feb. 25, 2015", 9 pgs.

"U.S. Appl. No. 13/038,987, Non Final Office Action dated May 19, 2014", 8 pgs.

"U.S. Appl. No. 13/038,987, Non Final Office Action dated Sep. 10, 2013", 7 pgs.

"U.S. Appl. No. 13/038,987, Notice of Allowance dated Oct. 23, 2015", 10 pgs.

"U.S. Appl. No. 13/038,987, Response filed Jan. 5, 2015 to Final Office Action dated Nov. 5, 2014", 9 pgs.

"U.S. Appl. No. 13/038,987, Response filed Feb. 5, 2015 to Advisory Action dated Jan. 23, 2015", 9 pgs.

"U.S. Appl. No. 13/038,987, Response filed Apr. 7, 2014 to Final Office Action dated Feb. 7, 2014", 8 pgs.

"U.S. Appl. No. 13/038,987, Response filed Aug. 19, 2014 to Non Final Office Action dated May 19, 2014", 8 pgs.

"U.S. Appl. No. 13/038,987, Response filed Sep. 16, 2015 to Final Office Action dated Jun. 16, 2015", 9 pgs.

"U.S. Appl. No. 13/038,987, Response filed Dec. 9, 2013 to Non Final Office Action dated Sep. 10, 2013", 9 pgs.

"U.S. Appl. No. 13038,987, Response filed May 26, 2015 to Non Final Office Action dated Feb. 25, 2015", 9 pgs.

Park, Sang-Shik, et al., "Anodizing Properties of High Dielectric Oxide Films Coated on Aluminum by Sol-Gel Method", Journal of Electroceramics 13, (2004), 111-116.

Watanabe, Keiji, et al., "Formation of Al—Zr composite oxide films on aluminum by sol-gel coating and anodizing", Journal of Electroanalytical Chemistry 473, (1999), 250-255.

* cited by examiner

SYSTEMS AND METHODS FOR ENHANCED DIELECTRIC PROPERTIES FOR ELECTROLYTIC CAPACITORS

CLAIM OF PRIORITY

This application is a continuation of U.S. application serial No. 13/038,987, filed Mar 2, 2011, now issued as U.S. Pat. No. 9,275,801, which claims the benefit of priority under 35 U.S.C. § 119(e) of U.S. Provisional Patent Application Serial Number 61/315,586, filed on Mar. 19, 2010, each of which is herein incorporated by reference in its entirety.

TECHNICAL FIELD

This document relates generally to energy storage and particularly to enhanced dielectric properties for electrolytic capacitors to store energy in an implantable medical device.

BACKGROUND

Electrical stimulation therapy has been found to benefit some patients. For example, some patients suffer from an irregular heartbeat or arrhythmia and may benefit from application of electrical stimulation to the heart. Some patients suffer from a particular type of arrhythmia called a fibrillation. Fibrillations may affect different regions of the heart, such as the atria or the ventricles. When a fibrillation occurs in the ventricles, the heart's ability to pump blood is dramatically reduced, putting the patient at risk of harm. It has been found that applying an electrical stimulation to the patient can effectively treat patients suffering disorders such as from fibrillation by restoring a regular heartbeat.

Because disorders such as fibrillations can happen at any time, it is helpful to have a device that is easily accessible to treat them. In some cases, it is helpful if that device is portable or implantable. In developing a device that is portable or implantable, it is helpful to have access to subcomponents that are compact and lightweight and that can perform to desired specifications.

SUMMARY

This disclosure relates to apparatus for enhanced dielectric properties for electrolytic capacitors to store energy in an implantable medical device. A capacitor according to one embodiment includes an anode, a cathode, and a dielectric separating the anode and the cathode. The dielectric comprises aluminum oxide doped with a metal oxide having a dielectric constant greater than aluminum oxide, in various embodiments.

An apparatus according to one embodiment includes an implantable device housing and a capacitor disposed in the implantable device housing. The capacitor includes a dielectric comprising aluminum oxide doped with an oxide having a dielectric constant greater than aluminum oxide, the dielectric separating an anode from a cathode. An embodiment of the apparatus includes pulse control electronics disposed in the implantable device housing and connected to the capacitor.

One aspect of the present subject matter includes a method for manufacturing a capacitor adapted to be disposed in an implantable device housing. An embodiment of the method includes providing a dielectric comprising aluminum oxide and doping the aluminum oxide with a metal oxide having a dielectric constant greater than aluminum oxide. Doping the aluminum oxide includes, but is not limited to, using sol-gel based chemistry, electrodeposition, mist deposition or atomic layer deposition (ALD) in various embodiments.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than an embodiment. The following detailed description is, therefore, not to be taken in a limiting sense, and the scope is defined only by the appended claims, along with the full scope of legal equivalents to which such claims are entitled.

Energy storage capacitors are used with implantable devices to provide stimulation energy. What is needed is to increase the energy storage of such capacitors while also reducing the size of the capacitors. The present disclosure relates to energy storage devices that include enhanced dielectric properties for electrolytic capacitors to store energy in an implantable medical device. An apparatus according to one embodiment includes an implantable device housing and a capacitor disposed in the implantable device housing. The capacitor includes a dielectric comprising aluminum oxide doped with an oxide having a dielectric constant greater than the dielectric constant of aluminum oxide, the dielectric separating an anode from a cathode. A capacitance and energy density increase is realized by doping the aluminum oxide of capacitor anodes. This doping results in a reduction in the volume of the capacitor needed for the same energy storage capacity.

Figure 1:
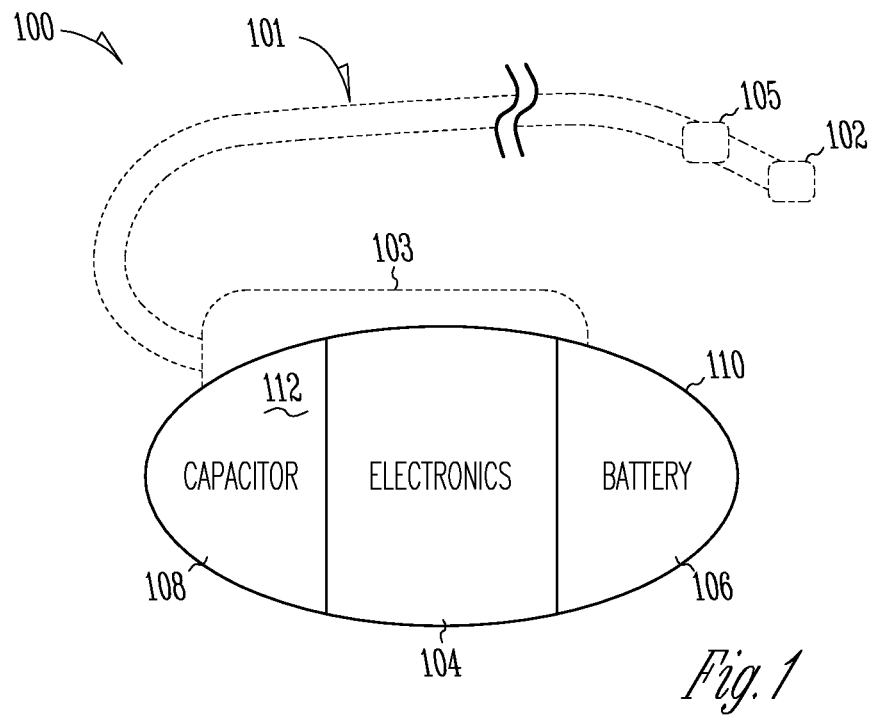
FIG. 1 is a schematic of a medical system including a capacitor having a doped dielectric, according to some embodiments.

FIG. 1 is a schematic of a medical system 100 including a capacitor having a doped dielectric, according to some embodiments. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

Electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. The electronics 104 can be recharged wirelessly using an inductor. Alternatively, the electronics 104 can be powered by a battery 106. In some examples, electronics 104 are to direct small therapeutic bursts of energy to a patient from the battery 106.

For therapies, such as defibrillation, that use energy discharge rates exceeding what battery 106 is able to provide, a capacitor 108 is used. Energy from the battery 106 is controlled by the electronics 104 to charge the capacitor 108. The capacitor 108 is controlled by the electronics 104 to discharge to a patient to treat the patient. In some examples, the capacitor 108 is switched on to provide therapeutic energy and switched off to truncate therapy delivery.

Some examples of a medical system 100 include a lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101. Leadless examples can be positioned in contact with the tissue to be stimulated, or can be positioned proximal to tissue to shock the tissue to be stimulated through intermediary tissue. Leadless examples can be easier to implant and can be less expensive as they do not require the additional lead components.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a cathode sized to deliver a defibrillation pulse of a desired amount of energy. In some examples, the energy level is predetermined to achieve a delivered energy level mandated by a governing body or standard associated with a geographic region, such as a European country. In some examples, this is the energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used.

Packaging anodes and cathodes can reduce their efficiency. Interconnections between conductors coupled to electronics and to the electrodes of the capacitor 108 decrease efficiency, for example. Accordingly, anodes and cathodes are sized to compensate for decreases in efficiency. As such, in some embodiments, the capacitor 108 includes anodes and cathodes sized and packaged to deliver a defibrillation pulse of at least approximately 50 joules. Some are sized and packaged to deliver a defibrillation pulse of at least approximately 60 joules.

One characteristic of some doped dielectric capacitor examples is that at the capacitor has a DC capacitance that is approximately 16% greater than a DC capacitance for a capacitor of a non-doped dielectric capacitor that has 79.6 microfarads per cubic centimeter. In some examples, the doped dielectric capacitor has an AC capacitance of at least 85.1 microfarads per cubic centimeter.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal.

A hermetically sealed device housing 110 is used to house components, such as the battery 106, the electronics 104, and the capacitor 108. Hermeticity is provided by welding components into the hermetically sealed device housing 110, in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to applications where high-energy, high-voltage, or space-efficient capacitors are desirable, including, but not limited to, capacitors used for photographic flash equipment. The present subject matter extends to energy storage devices that benefit from high surface area electrodes including, but not limited to, aluminum. The electrodes described here can be incorporated into cylindrical capacitors that are wound, in addition to stacked or folded capacitors. Other capacitor configurations can by used without departing from the scope of this disclosure.

Figure 2:
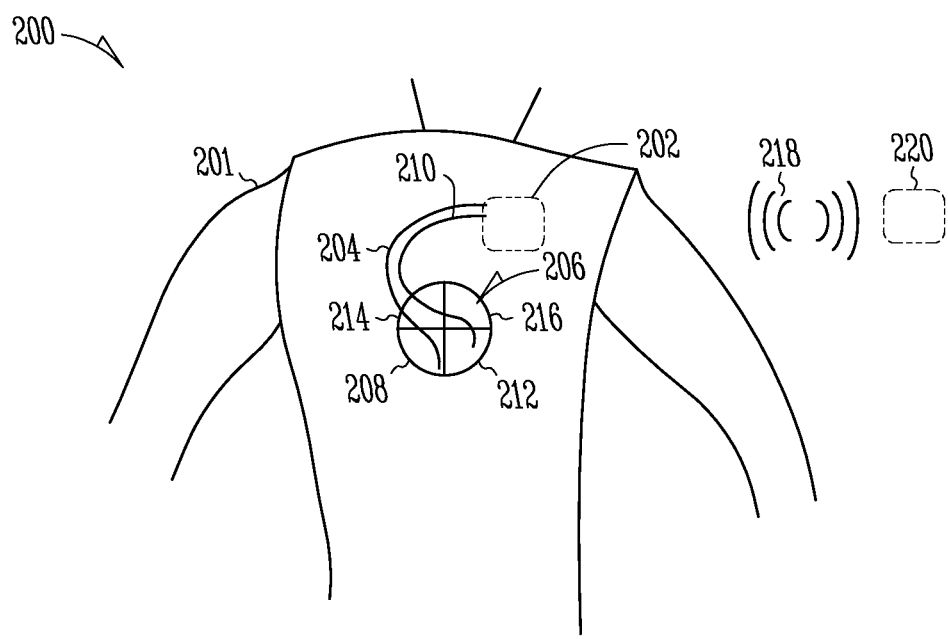
FIG. 2 is an implanted medical system including a capacitor having a doped dielectric, according to some embodiments.

FIG. 2 is an implanted medical system 200, implanted in a patient 201, and including a capacitor having a doped dielectric, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both those tissue regions. The second lead 210 is in direct contact with the left atrium 216 and the left ventricle 212 to sense and/or stimulate both those tissue regions. The cardiac rhythm management device 202 uses the lead electrodes to deliver energy to the heart, either between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

The capacitor includes an anode and a cathode separated by a dielectric. The capacitor may be coupled to electronics adapted to charge the capacitor and use the energy for various purposes such as delivering therapy via an implantable medical device. In various embodiments, the capacitor includes a doped dielectric. In various embodiments, a capacitor element includes a number of electrodes, including a number of cathode stacks and a number of anode layers. In various embodiments, the electrodes include foil, such as an aluminum foil.

An apparatus having enhanced dielectric properties for electrolytic capacitors to store energy in an implantable medical device is provided. An apparatus according to one embodiment includes an implantable device housing and a capacitor disposed in the implantable device housing. The capacitor includes a dielectric comprising aluminum oxide doped with a metal oxide having a dielectric constant greater than aluminum oxide, the dielectric separating an anode from a cathode. An embodiment of the apparatus includes pulse control electronics disposed in the implantable device housing and connected to the capacitor. The implantable device housing includes a defibrillator housing or a pacemaker housing, in various embodiments.

According to various embodiments, the oxide dopant that is to be integrated into the aluminum oxide is selected from the transition metal oxides listed in the Periodic Table of elements. The dielectric constant of these metal oxides is higher compared to aluminum oxide alone, and integration of these oxides into the aluminum increases the capacitance of the anodes. According to various embodiments, the metal oxide includes titanium oxide, zirconium oxide, cobalt oxide, hafnium oxide, silicon oxide, tantalum oxide, niobium oxide, and/or tungsten oxide. According to various embodiments, the oxide dopant includes a metal oxide, a mixed metal oxide, an oxy-hydroxide, and/or a metal hydroxide. An example of a mixed metal oxide includes barium titanate ($BaTiO_3$). Other oxide dopants can be used without departing from the scope of this disclosure.

Figure 3A:
FIG. 3A illustrates a dielectric layer for a capacitive element.
Figure 3B:
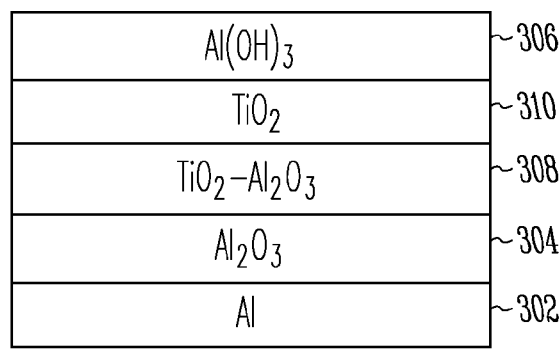
FIG. 3B illustrates a dielectric layer for a capacitive element, the dielectric layer including a coated material.

FIG. 3A illustrates a dielectric layer for a capacitive element. The depicted foil element includes an electrode 302. The electrode 302 can be any metal, but is shown as aluminum (Al). A dielectric layer 304 of aluminum oxide ($Al_2O_3$) is formed on the electrode, and a layer of aluminum hydroxide ($Al(OH)_3$) 306 is on the aluminum oxide layer. FIG. 3B illustrates a dielectric layer for a capacitive element, the dielectric layer including a coated material. The depicted foil element includes a higher dielectric material 310 coated on the dielectric layer. In this case, the higher dielectric material 310 is titanium oxide (TiO2). The titanium oxide and aluminum oxide are mixed in layer 308.

Figure 3C:
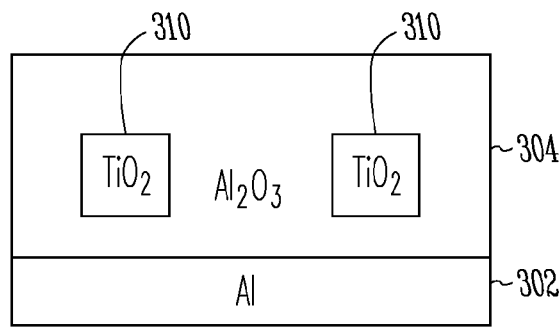
FIG. 3C illustrates a dielectric layer for a capacitive element, the dielectric layer including a doped material, according to various embodiments of the present subject matter.

FIG. 3C illustrates a dielectric layer for a capacitive element, the dielectric layer including a doped material, according to various embodiments of the present subject matter. The dielectric layer 304 of aluminum oxide has been doped with a higher dielectric material 310, so that the higher dielectric material is integrated into the aluminum oxide, according to the present subject matter. The present subject matter relates to techniques used to effectively add metal oxides having a relatively high dielectric constant to a base aluminum oxide (referred to as "doping") in an etched, porous anode used in a high voltage capacitor. According to various embodiments, the etching process is completed before the doping process to add surface area to the anode, but results in relatively high aspect ratio pores (e.g. 50:1) making it difficult to penetrate them with doping materials. Several techniques can be used to deposit doping materials into the pores of the anodes. Material is applied to foil with a variety of base oxide layers and electrochemically oxidized using the same process as the etched foil, in various embodiments. Further increases in capacitance and energy delivered are possible by enhancing sintered foil oxide technology using the present subject matter.

Figure 4A:
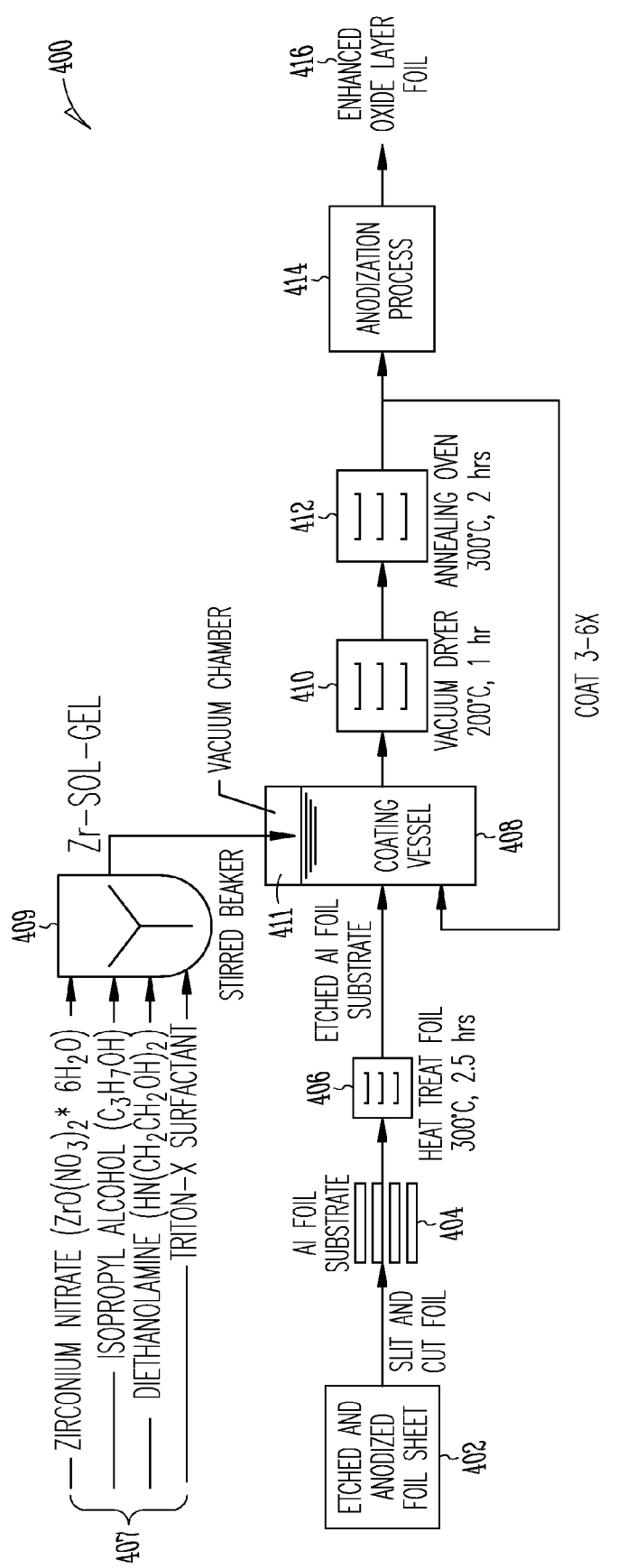
FIG. 4A illustrates a chemical solution deposition (sol-gel) process for doping a dielectric layer for a capacitive element, according to various embodiments.

FIG. 4A illustrates a chemical solution deposition (sol-gel) process for doping a dielectric layer for a capacitive element, according to various embodiments. The sol-gel process 400, also known as chemical solution deposition, is a wet-chemical technique used primarily for the fabrication of materials (typically a metal oxide) starting from a chemical solution which acts as the precursor for an integrated network (or gel in beaker 409) of either discrete particles or network polymers. Typical precursors are metal alkoxides and metal chlorides, which undergo various forms of hydrolysis and polycondensation reactions. The present subject matter involves using metal nitrates dissolved in alcohol or alkoxides diluted in alcohol as the precursors 407. These solutions 409 include diethanolamine and other organic compounds that assist in solvating metal ions such that the anodes can be dip coated 408 into volumes of the solution. The dip coating and drying can be repeated as needed, or three to six times in various embodiments. The dip coating includes using a vacuum chamber 411 for dip coating to remove air from the pores, in various embodiments. The anodes are first etched and anodized 402, slit and cut into foil 404, and heat treated 406. Heat treating includes heating at 300° C. for 2.5 hours, in an embodiment. Vacuum drying 410 removes the organic compounds and deposits a conformal coating of metal oxide particles on the surface. Vacuum drying includes drying at 200° C. for one hour, in an embodiment. Heat is applied using an annealing oven, at 412, to react the metal oxides together (calcination). The annealing oven is used at 300° C. for 2 hours, in an embodiment. Other temperatures and durations can be used without departing from the scope of the disclosure. The coated anode is anodized 414 using the appropriate voltage and aging electrolytes to integrate the dopants into the oxide of the anode. The resulting oxide layer 416 provides a capacitor with enhanced energy storage capability. In one embodiment of the sol-gel process, an electrophoresis coating 420 is applied as shown in FIG. 4B, the anode 430 is placed in a solution 422 and a voltage is applied 424 to provide a coating 426 on the anode.

Figure 4B:
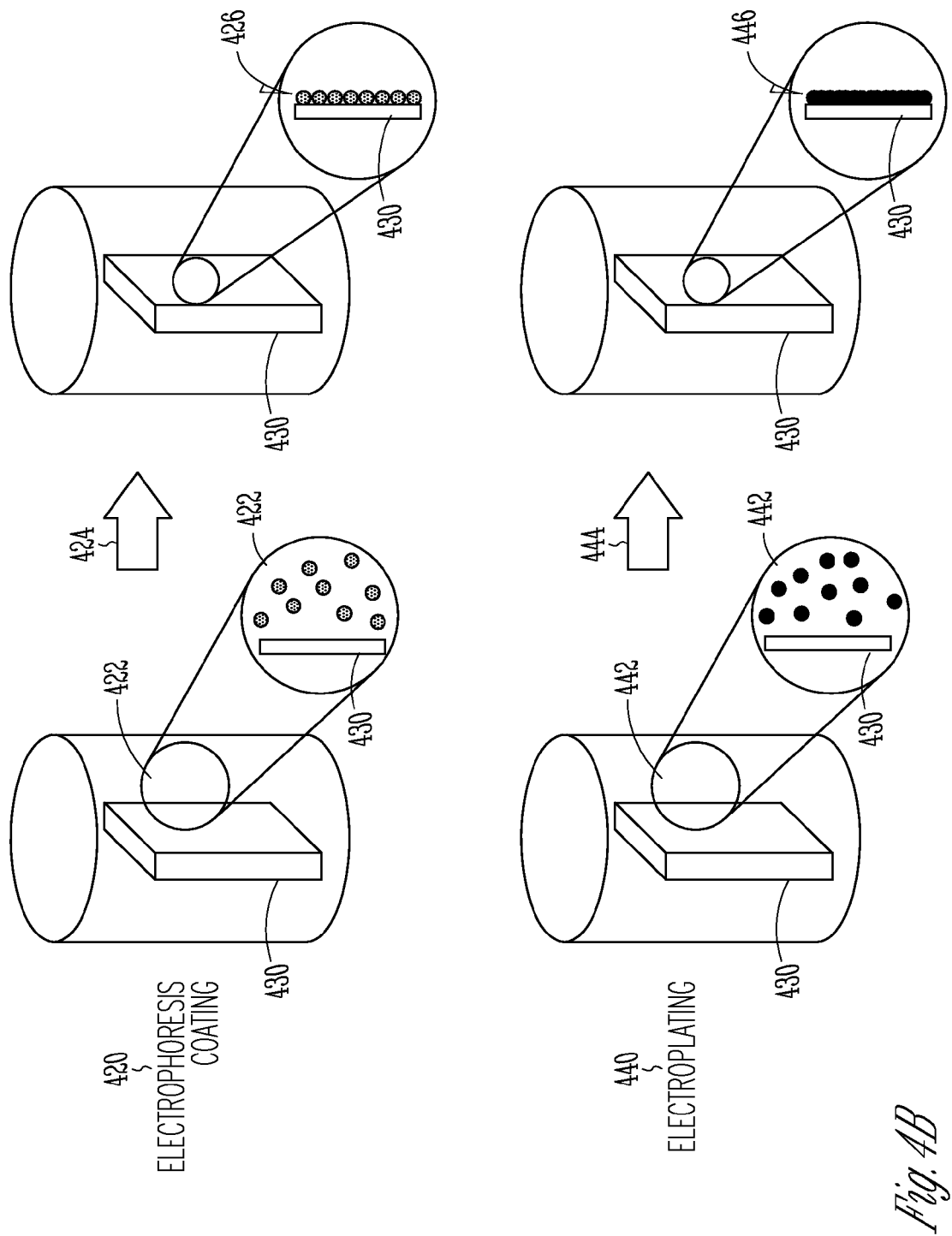
FIG. 4B illustrates an electrodeposition process for doping a dielectric layer for a capacitive element, according to various embodiments.

FIG. 4B illustrates an electrodeposition process for doping a dielectric layer for a capacitive element, according to various embodiments. Metal oxides, hydroxides, or other metal ion species can be deposited from aqueous, organic or mixed aqueous organic electrolyte solutions (422, 442). In an embodiment of electroplating 440, the anode 430 is placed in a solution 442 and a voltage is applied 444 to provide a plating 446 on the anode. In various embodiments, cathodic deposition of a metal hydroxide from a metal ion solution is provided by forming an excess of hydroxide ions at the surface of the aluminum or aluminum oxide. This local pH increase causes precipitation of metal oxides, hydroxides or mixed oxide-hydroxides. An embodiment includes a nitrate method where nitrate ion is reduced and leads to the formation of excess hydroxide ions. An embodiment of electrodeposition includes direct plating of a metal from a metal ion solution. Anodic deposition of a metal oxide, metal hydroxide or metal oxyhydroxide from solution is included in an embodiment. According to various embodiments, the plating baths may be aqueous, organic or mixed aqueous organic solutions. Various electrodeposition methods can be used without departing from the scope of the disclosure, including DC voltage or current, AC voltage or current, scanned voltage or current, or any combination thereof. The metal ion species can be deposited on the surface of the aluminum or aluminum oxide surfaces, in various embodiments. According to various embodiments, the metal ions species are incorporated into the aluminum oxide layer following the deposition process by heat treatment, such as annealing, or anodization of the aluminum, or a combination of annealing and anodization. A plurality of metal ion species can be deposited using the present subject matter.

Figure 4C:
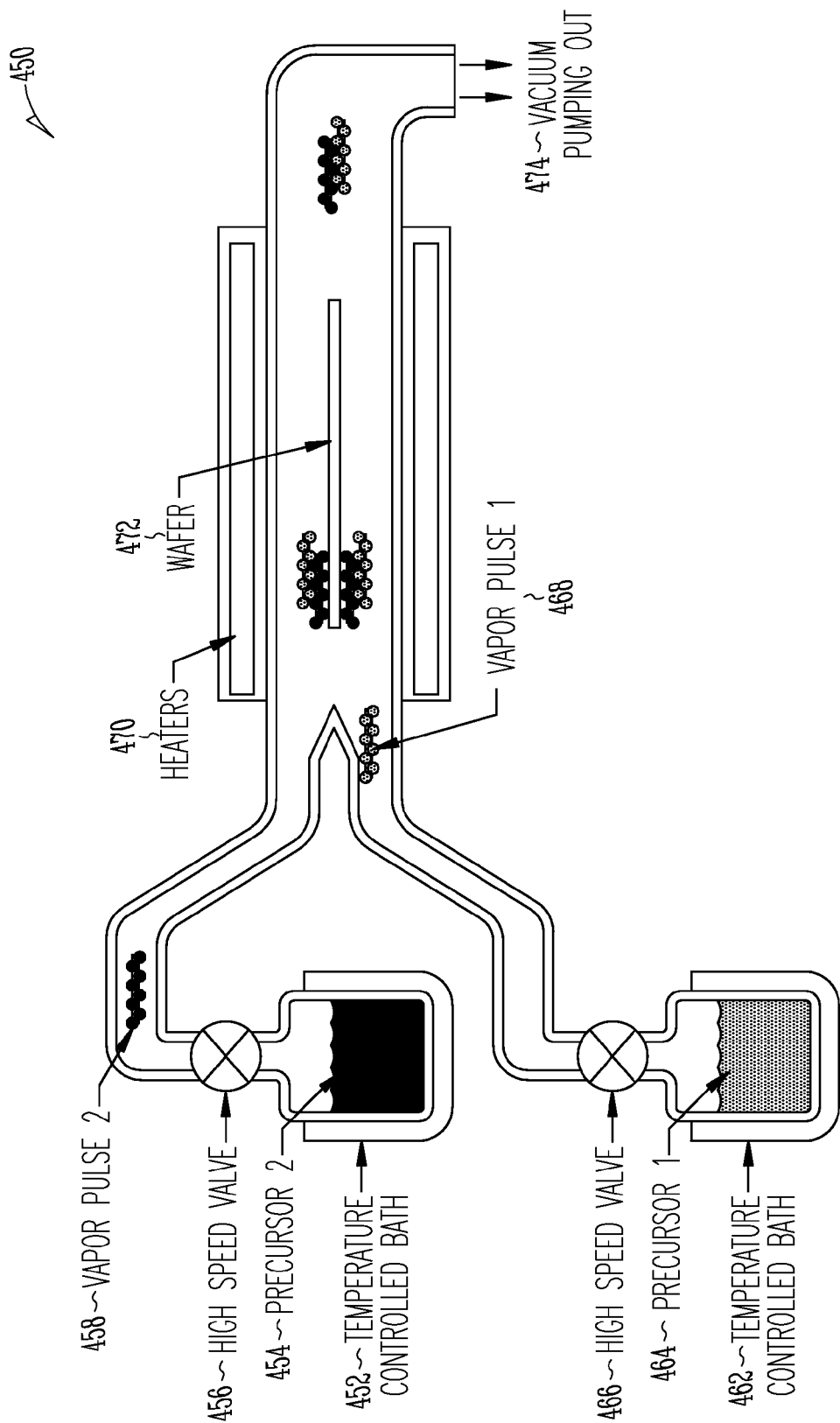
FIG. 4C illustrates an atomic layer deposition (ALD) process for doping a dielectric layer for a capacitive element, according to various embodiments.

FIG. 4C illustrates an atomic layer deposition (ALD) process 450 for doping a dielectric layer for a capacitive element, according to various embodiments. Metal ion species, including metal oxides, may be deposited using ALD. According to various embodiments, the process involves sequential deposition of two or more species from the vapor phase that react on the surface of a substrate to form the desired deposit. The depicted embodiment includes two species: a first temperature controlled bath 452 contains a first precursor 454 and a second temperature controlled bath 462 contains a second precursor 464 High speed valves 456 and 466 release vapor pulses 458 and 468 into water 472 heated using a heater 470, and is subsequently pumped out at vacuum pump 474. Single or multiple layers may be deposited in this way. The layers are uniform, thin and conformal to the substrate surface morphology, according to various embodiments. Examples of metal oxides that can be deposited using ALD include titanium, tantalum and hafnium oxides. Multiple layers of different metal oxides or single layers of mixed metal ion species can be deposited, in various embodiments. The metal ion species are deposited on the surface of the aluminum or aluminum oxide surfaces. According to various embodiments, the metal ion species can be incorporated into the aluminum oxide layer following the deposition process by heat treatment, such as annealing, or anodization of the aluminum, or a combination of annealing and anodization.

Figure 4D:
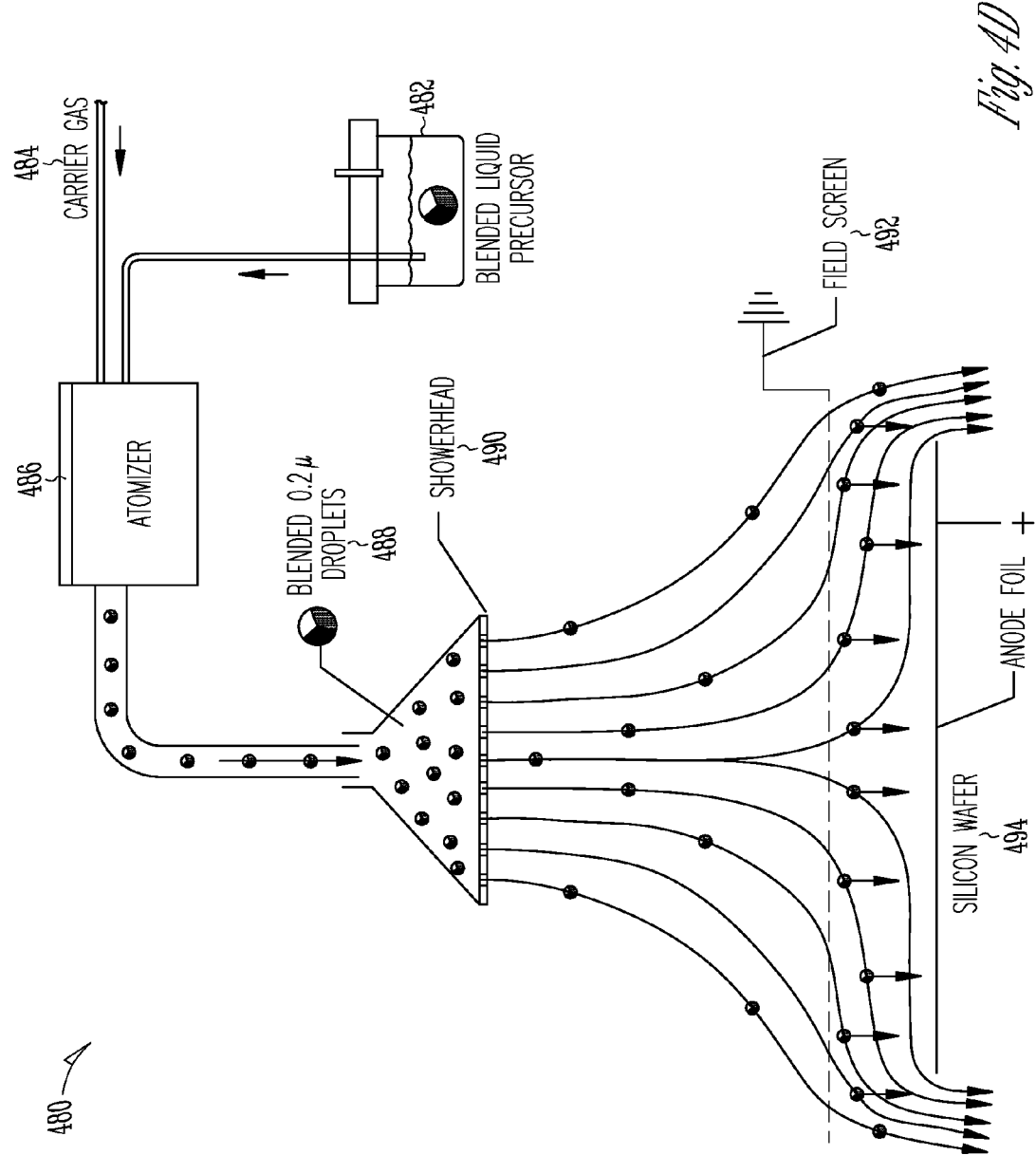
FIG. 4D illustrates a mist deposition process for doping a dielectric layer for a capacitive element, according to various embodiments.

FIG. 4D illustrates a mist deposition process 480 for doping a dielectric layer for a capacitive element, according to various embodiments. According to various embodiments, a blended liquid precursor 482 and a carrier gas 484 are combined in an atomizer 486. The resulting blended droplets 488 are dispensed from showerhead 490, passed through a field screen 492 and deposited on a silicon wafer (or anode foil) 494, according to various embodiments.

Figure 5:
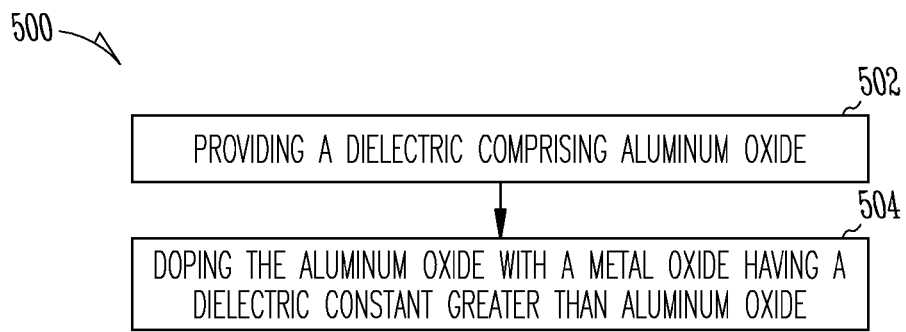
FIG. 5 illustrates a flow diagram of a method for manufacturing a capacitor adapted to be disposed in an implantable device housing, according to various embodiments.

FIG. 5 illustrates a flow diagram of a method for manufacturing a capacitor adapted to be disposed in an implantable device housing, according to various embodiments. An embodiment of the method 500 includes providing a dielectric comprising aluminum oxide, at 502, and doping the aluminum oxide with a metal oxide having a dielectric constant greater than aluminum oxide, at 504. Doping the aluminum oxide includes using sol-gel based chemistry (chemical solution deposition), electrodeposition, mist deposition or atomic layer deposition (ALD) in various embodiments.

According to various embodiments, using a sol-gel process to dope the aluminum oxide includes dip coating the dielectric in a metal ion solution including organic compounds, vacuum drying the dielectric, heating the dielectric to react the metal oxides, and anodizing the dielectric. According to various embodiments, using electrodeposition to dope the aluminum oxide includes cathodic deposition of a metal hydroxide from a metal ion solution. The electrodeposition includes direct cathodic plating of a metal from a metal ion solution, in an embodiment. In another embodiment, electrodeposition includes anodic deposition of a metal oxide from a solution.

Figure 6:
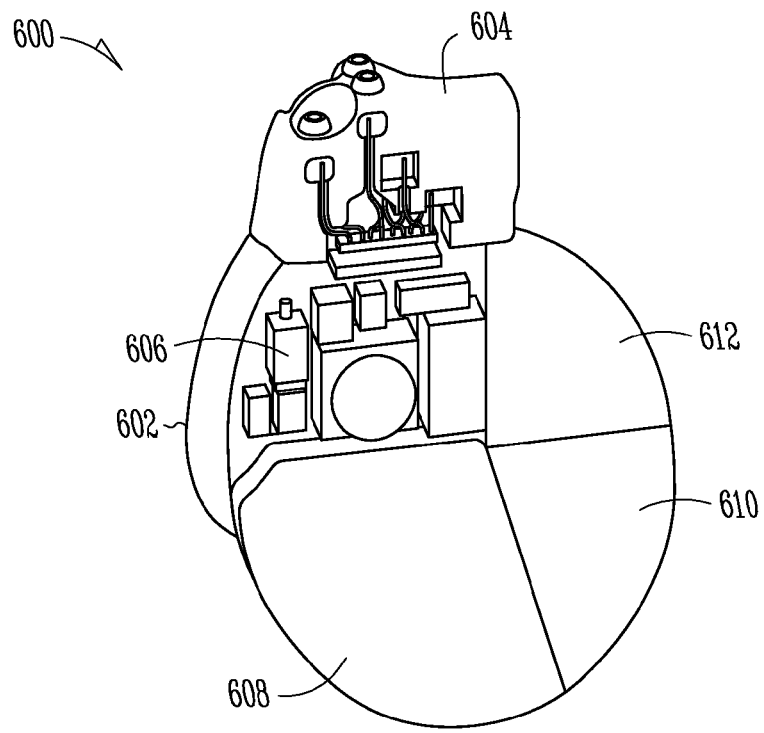
FIG. 6 illustrates an implantable medical system including a capacitor having a dielectric comprising doped aluminum oxide, according to various embodiments.

FIG. 6 illustrates an implantable medical system including a capacitor having a dielectric comprising doped aluminum oxide, according to various embodiments. The implantable medical system 600 includes a housing 602 and attached header 604. According to various embodiments, the housing 602 contains pulse control and communication electronics 606, a battery 608 and a storage capacitor 610. A capacitor manufactured using the present subject matter can provide the required energy storage capacity using a smaller volume. The depicted capacitor shows a 30% reduction in volume, which would reduce the volume by the amount shown at 612, in an embodiment. The present subject matter provides advantages for capacitor applications that benefit from increased energy density. The increase in energy density results in a smaller package size, and thus provides benefits to implantable medical devices. However, any application that combines high voltage capacitive storage with small size requirements would benefit from the present subject matter.

This application is intended to cover adaptations or variations of the present subject matter. It is to be understood that the above description is intended to be illustrative and not restrictive. The scope of the present subject matter should be determined with reference to the appended claims, along with the full scope of legal equivalents to which such claims are entitled.

What is claimed is:

1. A method for manufacturing a capacitor including a dielectric comprising aluminum oxide, the method comprising:
    using a vapor deposition process to dope the aluminum oxide with a plurality of metal oxides having a dielectric constant greater than aluminum oxide, wherein the doped aluminum oxide is distributed evenly throughout the entire thicknes, the dielectric, the dielectric in contact with an anode and a cathode and is configured to provide an increased energy storage capacity per volume for the capacitor.

2. The method of claim 1, comprising using sequential deposition of two or more species from a vapor phase that react on a surface of a substrate to form a desired deposit.

3. The method of claim 1, wherein doping the aluminum oxide with a metal oxide includes doping the aluminum oxide with titanium oxide.

4. The method of claim 1, wherein doping the aluminum oxide with a metal oxide includes doping the aluminum oxide with hafnium oxide.

5. The method of claim 1, wherein doping the aluminum oxide with a metal oxide includes doping the aluminum oxide with tantalum oxide.

6. The method of claim 1, wherein the metal oxide includes zirconium oxide.

7. The method of claim 1, wherein the metal oxide includes cobalt oxide.

8. The method of claim 1, wherein the metal oxide includes silicon oxide.

9. The method of claim 1, wherein the metal oxide includes tungsten oxide.

10. The method of claim 1, wherein the metal oxide includes niobium oxide.

11. The method of claim 1, wherein the oxide includes a mixed metal oxide.

12. The method of claim 11, wherein the mixed metal oxide includes barium titanate.

13. The method of claim 1, wherein the oxide includes an oxy-hydroxide.

14. The method of claim 1, wherein doping the aluminum oxide with a metal oxide includes using atomic layer deposition (ALD).

15. A method for manufacturing a capacitor including a dielectric comprising aluminum oxide, the method comprising:

using a chemical deposition process to dope the aluminum oxide with a plurality of metal oxides having a dielectric constant greater than aluminum oxide, wherein the plurality of oxides are integrated into the aluminum oxide, and wherein the doped aluminum oxide is distributed evenly throughout the entire thickness the dielectric, the dielectric in contact with an anode and a cathode and is configured to provide an increased energy storage capacity per volume for the capacitor.

16. The method of claim 15, wherein doping the aluminum oxide includes using a chemical solution deposition (sol-gel) process.

17. The method of claim 15, wherein doping the aluminum oxide includes using an electrophoretic deposition.

18. A method for manufacturing a capacitor including a dielectric comprising aluminum oxide, the method comprising:

using an electrodeposition process to dope the aluminum oxide with a plurality of metal oxides having a dielectric constant greater than aluminum oxide, wherein the doped aluminum oxide is distributed evenly throughout the entire thickness the dielectric, the dielectric in contact with an anode and a cathode and is configured to provide an increased energy storage capacity per volume for the capacitor.

19. The method of claim 18, wherein electrodeposition includes cathodic deposition of a metal hydroxide from a metal ion solution.

20. The method of claim 18, wherein electrodeposition includes direct cathodic plating of a metal from a metal ion solution.

* * * * *